(12) United States Patent
Varkuti et al.

(10) Patent No.: US 12,303,204 B2
(45) Date of Patent: May 20, 2025

(54) AUTOMATED PRE-OPERATIVE ASSESSMENT OF IMPLANT PLACEMENT IN HUMAN BONE

(71) Applicant: Brainlab AG, Munich (DE)

(72) Inventors: Bálint Varkuti, Munich (DE); Bogdan Moldovan, Munich (DE)

(73) Assignee: BRAINLAB AG, Munich (DE)

( * ) Notice: Subject to any disclaimer, the term of this patent is extended or adjusted under 35 U.S.C. 154(b) by 867 days.

(21) Appl. No.: 17/260,096

(22) PCT Filed: Aug. 30, 2018

(86) PCT No.: PCT/EP2018/073320
§ 371 (c)(1),
(2) Date: Jan. 13, 2021

(87) PCT Pub. No.: WO2020/043291
PCT Pub. Date: Mar. 5, 2020

(65) Prior Publication Data
US 2021/0322101 A1    Oct. 21, 2021

(51) Int. Cl.
*A61B 34/10*    (2016.01)
*A61B 34/00*    (2016.01)
(Continued)

(52) U.S. Cl.
CPC .............. *A61B 34/10* (2016.02); *A61B 34/25* (2016.02); *A61B 90/14* (2016.02);
(Continued)

(58) Field of Classification Search
CPC ......... A61B 34/10; A61B 34/25; A61B 90/14; A61B 2034/104; A61B 2034/105;
(Continued)

(56) References Cited

U.S. PATENT DOCUMENTS 6,086,533 A * 7/2000 Madsen ............... A61B 5/0053
                                                        600/561
7,783,359 B2   8/2010 Meadows
(Continued)

FOREIGN PATENT DOCUMENTS

WO   2006075331    7/2006
WO   2006092600    9/2006
(Continued)

OTHER PUBLICATIONS

Raudaschl, Patrik F., et al. "Evaluation of segmentation methods on head and neck CT: auto-segmentation challenge 2015." Medical physics 44.5 (2017): 2020-2036. (Year: 2017).*
(Continued)

*Primary Examiner* — Sean M Conner
*Assistant Examiner* — Stefano Anthony Dardano
(74) *Attorney, Agent, or Firm* — Gray Ice Higdon

(57) ABSTRACT

A computer-assisted and automatic identification of possible cranial positions for any kind of implant is presented. In this method, skull data of the individual patient's skull are used as well as statistical skull data which include so-called skull avoidance zones. Further, a digital template of the implant is used to find these possible positions. The implant may be e.g. an IPG and/or the screws of a fixation frame, but these are only embodiments of implants and other implants may be used with the present invention as well. The computer-implemented medical method of the present invention removes the uncertainty whether a given patient can safely receive an implant, like for example a cranial IPG, which was previously only possible on the basis of human judgement. Furthermore, the present invention removes the uncertainty whether a given patient can be safely fixated in a stereotactic frame or a Mayfield head clamp. The present invention supports the localization of optimal implant loca- (Continued)

tion as well as neuro-navigation guided execution of surgery. This enhances safety and speed of the entire medical procedure, as will be explained in more detail hereinafter. The advantages described hereinbefore are in the same way realized by the computer program, the medical system and the navigation system for computer-assisted surgery of the present invention.

23 Claims, 7 Drawing Sheets

(51) Int. Cl.
  *A61B 90/14*  (2016.01)
  *A61N 1/375*  (2006.01)
  *G06T 7/11*  (2017.01)
  *G06T 19/20*  (2011.01)
  *G06V 40/10*  (2022.01)
  *G16H 10/60*  (2018.01)
  *G16H 15/00*  (2018.01)
  *G16H 20/30*  (2018.01)
  *G16H 20/40*  (2018.01)
  *G16H 30/20*  (2018.01)
  *G16H 30/40*  (2018.01)
  *G16H 40/63*  (2018.01)
  *G16H 50/30*  (2018.01)

(52) U.S. Cl.
  CPC ............ *A61N 1/37514* (2017.08); *G06T 7/11* (2017.01); *G06T 19/20* (2013.01); *G06V 40/10* (2022.01); *G16H 10/60* (2018.01); *G16H 15/00* (2018.01); *G16H 20/30* (2018.01); *G16H 20/40* (2018.01); *G16H 30/20* (2018.01); *G16H 30/40* (2018.01); *G16H 40/63* (2018.01); *G16H 50/30* (2018.01); *A61B 2034/104* (2016.02); *A61B 2034/105* (2016.02); *G06T 2207/20128* (2013.01); *G06T 2210/41* (2013.01); *G06T 2219/2012* (2013.01); *G06V 2201/033* (2022.01)

(58) Field of Classification Search
  CPC ... A61B 5/1075; A61B 5/4509; A61B 5/4538; A61B 34/30; A61B 2034/2055; A61B 2034/102; A61B 5/686; A61B 34/20; A61N 1/37514; A61N 1/0534; A61N 1/0539; A61N 1/3605; G06T 7/11; G06T 19/20; G06T 2207/20128; G06T 2210/41; G06T 2219/2012; G06V 40/10; G06V 2201/033; G16H 10/60; G16H 15/00; G16H 20/30; G16H 20/40; G16H 30/20; G16H 30/40; G16H 40/63; G16H 50/30; A61F 2/2875

See application file for complete search history.

(56) References Cited

U.S. PATENT DOCUMENTS

| | | | | |
|---|---|---|---|---|
| 9,165,360 | B1* | 10/2015 | Bates | ........................ G06T 7/11 |
| 9,492,241 | B2* | 11/2016 | Joskowicz | ............. A61B 90/11 |
| 2002/0013612 | A1 | 1/2002 | Whitehurst | |
| 2004/0172090 | A1 | 9/2004 | Janzig et al. | |
| 2005/0245806 | A1* | 11/2005 | Singhal | ................ A61B 5/6864 |
| | | | | 600/407 |
| 2007/0225773 | A1 | 9/2007 | Shen et al. | |
| 2009/0177081 | A1* | 7/2009 | Joskowicz | ............. A61B 90/36 |
| | | | | 606/130 |
| 2019/0214126 | A1* | 7/2019 | Goetz | ..................... A61B 6/563 |
| 2020/0043168 | A1* | 2/2020 | Tanji | ..................... A61B 17/152 |

FOREIGN PATENT DOCUMENTS

| | | |
|---|---|---|
| WO | 2010068212 | 6/2010 |
| WO | 2015124199 | 8/2015 |
| WO | 2017039762 | 3/2017 |
| WO | 2019139690 A1 | 7/2019 |
| WO | 2020043291 | 3/2020 |

OTHER PUBLICATIONS

Labadie, Robert Frederick, et al. "Clinical validation of percutaneous cochlear implant surgery: initial report." The Laryngoscope 118.6 (2008): 1031-1039. (Year: 2008).*
Powell, Kimerly A., et al. "Atlas-based segmentation of temporal bone anatomy." International journal of computer assisted radiology and surgery 12 (2017): 1937-1944. (Year: 2017).*
Metzger, Marc Christian, et al. "Design and development of a virtual anatomic atlas of the human skull for automatic segmentation in computer-assisted surgery, preoperative planning, and navigation." International journal of computer assisted radiology and surgery 8.5 (2013): 691-702. (Year: 2013).*
Faisan, Sylvain, et al. "Topology preserving warping of binary images: Application to atlas-based skull segmentation." International Conference on Medical Image Computing and Computer-Assisted Intervention. Berlin, Heidelberg: Springer Berlin Heidelberg, 2008. (Year: 2008).*
Raudaschl, Patrik F., et al. "Evaluation of segmentation methods on head and neck CT: auto-segmentation challenge 2015." Medical physics 44.5 (2017): 2020-2036. (Year: 2015).*
Wimmer, Wilhelm, et al. "Topographic bone thickness maps for Bonebridge implantations." European Archives of Oto-Rhino-Laryngology 272 (2015): 1651-1658. (Year: 2015).*
International Search Report and Written Opinion for Application No. PCT/EP2018/073320 dated May 28, 2019. 12 pages.
European Patent Office; Communication issued in Application No. 18762285.7, 5 pages, dated Jun. 4, 2024.

* cited by examiner

AUTOMATED PRE-OPERATIVE ASSESSMENT OF IMPLANT PLACEMENT IN HUMAN BONE

FIELD OF THE INVENTION

The present invention relates to the planning of implanting medical implants into human bone. In particular, the present invention relates to a computer-implemented medical method of identifying a cranial position for an implant in a patient's skull, a computer program, a medical system, and a navigation system for computer-assisted surgery.

TECHNICAL BACKGROUND

Deep brain stimulation (DBS) is a neurosurgical procedure involving the implantation of a medical device called a neurostimulator or implantable pulse generator (IPG). Such devices are also referred to as a brain pacemaker. These devices send electrical impulses, through implanted electrodes, to specific targets in the brain for the treatment of movement and neuropsychiatric disorders. Such implantable pulse generators (IPGs) are nowadays placed in the abdominal cavity or in the chest cavity of the patient, which shall receive such a deep brain stimulation.

Furthermore, in stereotactic radiotherapy, a fixed headframe is typically used in order to securely and precisely fix the patient with respect to the treatment beam. In this context, a stereotactic fixation of the patient's skull with screws into the patient's skull is used in order to ensure precise immobility of the skull relative to the radiotherapy beam.

The inventors of the present invention have identified that there exists an uncertainty whether a given patient can safely receive e.g. such a cranial IPG, which in the prior art is only evaluated on the basis of human judgement. The same uncertainty is identified by the present inventors for the fixation of e.g. a stereotactic frame or a Mayfield head clamp.

Aspects of the present invention, embodiments, examples and exemplary steps are disclosed in the following. Different embodiments, examples and exemplary features of the invention can be combined in accordance with the invention wherever technically expedient and feasible.

It must be noted that the present invention can be used for any kind of navigation system for computer-assisted surgery, such as e.g. the Brainlab Cranial Navigation Application, which is a product of Brainlab AG.

EXEMPLARY SHORT DESCRIPTION OF THE INVENTION

In the light of the prior art described herein, it may be seen as the object of the present invention to provide for an improved identification of one or more cranial positions for an implant in a patient's skull.

In the following, a short description of the specific features of the present invention is given which shall not be understood to limit the invention only to the features or a combination of the features described in this section. An automated pre-operative assessment of implant placement in a human bone, particularly the human skull, is presented.

In particular, a computer-assisted and automatic identification of possible cranial positions for any kind of implant is presented. In this method, skull data of the individual patient's skull are used as well as statistical skull data which include so-called skull avoidance zones, as will be explained in more detail hereinafter. Further, a digital template of the implant is used to find these possible positions. The implant may be e.g. an IPG and/or the screws of a fixation frame, but these are only embodiments of implants and other implants may be used with the present invention as well.

The computer-implemented medical method of the present invention removes the uncertainty whether a given patient can safely receive an implant, like for example a cranial IPG, which was previously only possible on the basis of human judgement. Furthermore, the present invention removes the uncertainty whether a given patient can be safely fixated in a stereotactic frame or a Mayfield head clamp. The present invention supports the localization of optimal implant location as well as neuro-navigation guided execution of surgery. This enhances safety and speed of the entire medical procedure, as will be explained in more detail hereinafter. The advantages described herein before are in the same way realized by the computer program, the medical system and the navigation system for computer-assisted surgery of the present invention.

The inventors of the present invention expect that in deep brain stimulation, a new generation of implantable pulse generators will be brought into the market, which (most rechargeable) are not placed in abdominal or chest cavity anymore, but are anchored in or on top of the skull. These devices can have a thickness of below 1 cm. However, not every skull has bone regions that are thick enough to safely accommodate the full or even partial depth of such an implant. Also beyond implant size, skull thickness and no go zones on the cranium are of interest for the placement of stereotactic frames or Mayfield clamps in general neurosurgery. Specifically, in pediatric patients where there is no sufficient information on bone density, any type of additional information on where to place things on or within the bone can be of great benefit. The present invention provides important information about this as will become apparent from the following explanation.

In particular, the method of the present invention uses automatic detection of skull thickness and/or density under active exclusion of certain statistical or rule-based skull exclusion/skull avoidance zones. Such avoidance zones are for example the sides of the head for muscles, the back of the head because of patients need to be able to lie down, and/or the front of the skull because of sinuses. The automatic detection of skull thickness can be done by computerized segmentation as will be explained in more detail herein below. The method may further make use of cranial implant fitting using a geometrical description of the implant when calculating one more cranial positions or regions. These calculated positions or regions are outside of said skull avoidance zones or at least have only a predefined overlap with said regions, as previously defined by the user.

In general, the presented method can already during pre-operative planning help the surgeons choose whether to implant the desired implant in these patient. In an embodiment, the method may be used to also generate a suggestion which implant shall be used for the individual patient under the constraints given by the individual skull that is analysed. Thus, the present invention beneficially supports the decision for the surgeon where to do the implantation, and/or which implant can be safely used. It can also aid the surgeon in e.g. planning pre-operatively where and how to place frames and head clamps in the safest possible manner.

In particular embodiments of the presented method, the extraction of skull thickness data from MRI images by means of universal atlas segmentation is provided in combination with explicit 3-dimensional template fitting of implant models, like for example IPG models. Moreover, in specific embodiments, Augmented Reality can be used to visualize the result of the computer-implemented medical method presented herein. This will be explained in more detail herein below.

GENERAL DESCRIPTION OF THE INVENTION

In the following section, a description of the general features of the present invention is given, for example by referring to possible embodiments of the invention.

As stated above, it may be desirable to provide for an improved identification of a cranial position for an implant in a patient's skull.

This is achieved by the subject-matter of the independent claims, wherein further embodiments are incorporated in the dependent claims and the following description.

The described embodiments similarly pertain to the method of identifying a cranial position for an implant in a patient's skull, the computer program, the medical system and the navigation system for computer-assisted surgery. Synergetic effects may arise from different combinations of the embodiments although they might not be described in detail hereinafter. Furthermore, it shall be noted that all embodiments of the present invention concerning the method might be carried out in the order of the steps as explicitly described herein. Nevertheless, this has not to be the only and essential order of the steps of the method. The herein presented methods can be carried out in another order of the disclosed steps without departing from the respective method embodiment, unless explicitly mentioned to the contrary hereinafter.

Technical terms are used by their common sense. If a specific meaning is conveyed to a certain term, definitions of terms will be given in the following in the context of which the terms are used.

According to a first aspect of the present invention, a computer-implemented medical method of identifying a cranial position for an implant in a patient's skull is presented. The method comprises the step of acquiring an individual patient data set which describes a bone thickness and/or a bone density of the patients skull. Furthermore, the step of acquiring statistical skull data including skull avoidance zones in which no implant shall be implanted is comprised by the method. The step of acquiring a digital template data set which geometrically describes at least one implant is also comprised. Further the step of automatically identifying possible cranial positions on the patient's skull for the at least one implant based on the individual patient data set and the statistical skull data thereby using the geometrical description of the at least one implant is part of this computer-implemented medical method.

In other words, an automated pre-operative assessment of implant placement in human skull bone is presented. This automated and computer-implemented method combines statistical information or rule-based information with the individual patient data, which describes the skull thickness and/or the bone density of the patient's skull. In this way, the presented method removes uncertainty whether a given patient can for example safely receive a cranial implant. Therefore, in supporting localization of optimal implant location the presented method enhances safety and the overall speed of the medical procedure, since with regards to skull thickness and frame placement, the practitioners before the present invention was made have been relying on experience alone. The result calculated by the presented method, i.e. the identified possible cranial positions, can be beneficially used for neuro-navigation guided execution of surgery.

As becomes apparent for the skilled reader from the present disclosure, the presented method may be applied to any kind of implant. Exemplary embodiments of such an implant are the previously mentioned implantable pulse generator (IPG) or screws of a fixation frame for stereotactic therapy.

In general, the method may identify at least one cranial position but may of course also identify a plurality of cranial positions which can be suggested to the user for using them during the implantation of the implant. In particular, such a cranial position may define an area and/or a 3-dimensional volume in the individual patient's skull where the implant, e.g. the IPG, can be securely implanted. An exemplary non-limiting example of such a calculated cranial position in the sense of a 3-dimensional skull volume, which can be removed in order to provide a recess for the implant, can be gathered from and will be described in more detail in the context of FIG. 7.

It must be noted that the features of the present presented method relating to "acquiring a data set" or "acquiring data" broadly covers both the retrieval of an existing data set from e.g. a computer or server, as well as the generation of such a data set. This will also be further elucidated in the context of further exemplary embodiments. In particular, the extraction of skull/bone thickness data and/or density data of the individual patient's skull from medical images of the individual patient, particularly from MRI images from the individual patient, may be used for the method step of acquiring the individual patient data set. Such an extraction of the bone thickness and/or bone density data of the individual patient's skull from medical images may use in an embodiment universal atlas segmentation, as will be described in more detail hereinafter.

In an exemplary embodiment of the step of acquiring the individual patient data set, CT and/or MRI images are acquired and are sent to the device carrying out this computer-implemented medical method. Furthermore, a universal atlas automatic segmentation can be run to extract the skull of the individual patient. The skull density and/or the skull thickness can be determined based on the result of extracting the skull from the acquired CT and/or MRI images. If desired, also a fontanelles detection can be carried out which can contain the possibility to determine in pediatric cases whether the fontanelles are closed or open. If desired, also the sinuses and possible calcifications can be detected in an exemplary embodiment of the step of acquiring the individual patient data set. All the corresponding results of these possibilities may be stored alone or in combination in the individual patient data set acquired during the method described herein.

As has been explained hereinbefore, the computer-implemented medical method takes into account skull avoidance zones. The statistical skull data used in the method presented herein in this way uses and takes into account geometrical restrictions for possible cranial positions for the implant which are suggested or presented to the user as a result of the presented method. These geometrical constraints or limitations describe certain areas of a so to say "statistical" human skull which shall be excluded for the search or calculation algorithm when identifying said possible cranial positions or regions. These geometrical constraints may originate from medical statistics e.g. stored in a database and/or may be received as a user input to for example a user interface thereby transferring the knowledge and experience of the user to the device carrying out the presented method. In general, these geometrical constraints or limitations shall be excluded from suggesting to the user possible cranial positions for implantation. Therefore, such geometrical constraints are termed herein skull avoidance zones.

Preferably, such skull avoidance zones may comprise the sides of the skull where muscles are located, the back of the skull because the patient needs to be able to lay down and shall not be hampered by an implant positioned at such a back position of the skull, information that can be used describing the typical or individual hairline position to avoid aesthetic disfigurement, and statistical information on typical position and/or size of the inter-individually variable frontal sinuses.

For the step of acquiring a digital template data set geometrically describing the at least one implant, a system carrying out the method may automatically retrieve such data from e.g. a data storage where such data are stored. However, the system may also ask a user for providing such data via a user interface, e.g. a graphical user interface.

In a particular embodiment, the method described herein may also process a minimum skill thickness value under the implant required to maintain stable skull properties. In such an embodiment, this information may also be acquired from for example a database and/or may be provided via a user interface. The corresponding system may thus require the user to provide for such an information regarding the minimum skull thickness under the implant. This will be described in more detail hereinafter.

Furthermore, in the automatic process of identifying possible cranial positions on the patient's skull, the method detects geometrical areas in which the at least one implant may be placed without having any or at least only an acceptable overlap with said skull avoidance zones. The computer-implemented medical method may thus apply a template fitting on the individual patient data set describing the skull such that the at least one implant can be securely placed on that skull without interfering with the skull avoidance zones. In the particular embodiment where the minimum skull thickness value is also taken into account, the computer-implemented medical method only applies such a template fitting in the skull areas where the minimum skull thickness is met and which lie outside of the skull avoidance zones. During such a template fitting, data geometrically describing the implant are used to fit this calculative representation of the implant into the individual skull. In particular, in the context of IPG placement into the skull, it must be noted that bone shall be removed from the skull providing for a geometrically defined recession (as so referred to herein as "IPB bed") in order to then receive in that recession the IPG to be implanted. This will be described in more detail hereinafter in the context of FIG. 7 in which such an IPB bed is schematically shown.

After the automatic identification of one or more possible cranial positions, it can preferably be displayed to the user whether a cranial implantation is safely possible for the selected implant. Furthermore, in an embodiment, a feedback may be provided to the user if implantation is nowhere possible. In such an embodiment, the system may also suggest and prompt alternative implants. For example, the computer-implemented medical method may search within a database describing several different implants and may suggest an alternative implant selection to the user, which may fit with respect to the individual patient data set and the acquired statistical skull data. The results of the automatic identification of one or more possible cranial positions may be displayed to the user such that the areas are identified, for example using color-coding, where implantation can be done. This embodiment of the present invention can also be gathered from the description of FIG. 3.

In another exemplary embodiment, a user input, which selects from the identified cranial positions or areas the one preferred by the user, is sent to a device like for example to an IGS neuro-navigation system and/or an Augmented Reality display. This may then be used for supporting implantation. The identified and selected possible cranial position may also be sent to a robot to automatically commence milling, for example to provide for a cranial IPG bed on a stereotactically fixated skull.

As has been described herein before in great detail, such a computer-implemented medical method allows for an automated pre-operative assessment of implant placement in human bone, particularly for pulse generator placement in human skull. This method removes the uncertainty whether a given patient can safely receive the implant, preferably a cranial IPG, which was previously only carried out on the basis of individual and error-prone human judgement. The method thus enhances the accuracy in finding optimal implant location and thus enhances patient safety and accelerations the medical workflow.

An additional output that might be provided by the present invention is for example that a cranial positioning of the IPG desired by the user does not work in a secure manner. The method may therefore generate a suggestion that a dominal placement of the IPG shall be used. The suggestion may further contain information whether a rechargeable or a non-rechargeable IPG shall be used.

In an exemplary embodiment, the acquired individual patient data set and the acquired statistical skull data can be superimposed and can be visualized to the user. The superimposing of the statistical skull data on the individual patient data set may make use of elastic fusion, image fusion, image morphing and/or rigid image fusion, as will be defined in great detail hereinafter.

Furthermore, the user may provide an input with respect to a skull thickness required to hold the implant, for example a pin for a skull fixation (frame or clamp). This user input may be further processed by the computer-implemented medical method and may be taken into account during the identification of possible cranial positions, as will be explained in more detail hereinafter.

In the following, definitions of some terms used in the context of the first aspect of the present invention are provided.

Computer Implemented Method

The method in accordance with the invention is a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system, which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services, which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application, which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device, which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the following, preferred embodiments will be described in more detail.

According to an exemplary embodiment of the present invention, the step of automatically identifying possible cranial positions on the patient's skull comprises a 3-dimensional template fitting of the at least one implant.

In other words, the acquired digital template data set geometrically describes in 3-dimension the size and/or form of the at least one implant. This can of course also be carried out for several implants. These 3-dimensional data describing the form and/or size of the implant are then compared with the geometrical restrictions, which were acquired by receiving or retrieving the statistical skull data. In other words, in this embodiment, the computer-implemented medical method determines the contiguous area or areas of the individual patient's skull in which the implantation of said device is allowed when taking into account the constraints of the skull avoidance zones. In a further exemplary embodiment, such contiguous areas of the skull are determined after receiving the minimum thickness value, either from a retrieval from a data storage or from a user input, and the identification step of method takes such minimum skull thickness value into account. If desired, the presented method may also take into account a value of how much the implant, preferably an IPG, may extend above the surface of the skull after being implanted into the skull. Such a spatial extension of an IPG over and above the skull surface can be easily imagined when studying the exemplary embodiment described and shown in FIG. 7.

According to another exemplary embodiment of the present invention, the method further comprises the step of retrieving a minimum skull thickness under the implant required to maintain stable skull properties and/or retrieving a minimum skull thickness required to hold the implant for skull fixation.

The parameters retrieved in this embodiment are of particular importance for IPG implantation and in this case of fixating a stereotactic frame or a Mayfield head clamp at the patient's skull. In particular, beyond implant size also skull thickness and skull avoidance zones on the cranium are of interest for the placement of stereotactic frames or Mayfield clamps in general neurosurgery. This holds particularly true for pediatric patients where there is no sufficient information on bone density, any type of additional information on where to place things on or within the bone can be of great benefit. Therefore, in an advantageous embodiment, automatic detection of skull thickness under active exclusion of certain statistical or rule-based skull avoidance zones via for example universal atlas automatic segmentation and cranial IPG template fitting can already, during pre-operative planning help the user to choose whether to implant a cranial or conventional IPG in these patients. This of course supports the decision where to in fact implant the IPG. It can also aid the user in planning pre-operatively where and how to place frames and head clamps in the fastest possible manner.

According to another exemplary embodiment, the method further comprises the step of determining at least one continuous segment of the skull in which the retrieved minimum skull thickness is method. Furthermore, the step of automatically identifying possible cranial positions on the patient's skull is only carried out in said at least one determined segment which meets the minimum skull thickness determined previously.

Also a plurality of segments may meet the minimum skull thickness criterion. It is apparent to the skilled reader that the step of automatically identifying possible cranial positions is then carried out in all these segments, which meet the minimum skull thickness determined previously. This can be gathered from e.g. FIG. 3.

According to another exemplary embodiment of the present invention, the individual patient data set and the statistical skull data are provided in form of image data. In this embodiment, the method further comprises the steps of superimposing the individual patient data set with the statistical skull data in form of an image fusion of the individual patient data set and the statistical skull data.

For example, the MRI or CT images may be used. Furthermore, elastic fusion, image fusion/morphing, rigid fusion may be used. In the following, definitions of some terms used in this context of the present invention are provided.

Elastic Fusion, Image Fusion/Morphing, Rigid

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

According to another exemplary embodiment of the present invention, the method further comprises the step of displaying the respectively identified possible cranial position on a user interface, preferably using color coding in a graphical representation of the patient's skull.

In other words, in this embodiment, the results of the method are graphically displayed to the user by means of for example color coding. In particular, the contiguous areas, which were calculated as possible cranial positions to be used by the user for implantation, can be differentiated by the user due to the different graphical representations and/or color. Thus, other graphical representations and/or colors can be used for the possible positions/areas than for the skull avoidance zones and for the regions, which do not meet the requirements taken into account for identifying said possible positions/areas. Further details hereabout can be easily gathered from the exemplary embodiment described in the context of FIG. 3.

According to another exemplary embodiment of the present invention, the method comprises the acquisition of a CT image, an MRI image and/or at least one other medical image from the patient and extracting the patient's skull from the acquired images based on auto-segmentation. Furthermore, in this embodiment, the generation of the individual patient data set by determining the bone thickness and/or the bone density of the extracted patient's skull is comprised.

Pre-operative or intra-operative images may be captured. Using such pictures a universal atlas automatic segmentation may be run to extract the skull of the individual patient. Moreover, determining skull density and/or thickness from the extracted skull is then carried out. In a further exemplary embodiment, also the computerized detection of fontanelles, sinuses and calcification can be added.

In the following, definitions of some terms used in this context of the present invention are provided.
Atlas/Atlas Segmentation Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

According to another exemplary embodiment of the present invention, the method comprises the inquiring of a user input about which implant or implants are available for the implantation in the individual case of the patient. Furthermore, digital templates of the available implants within the digital template data set are provided.

The computer-implemented medical method of this embodiment may thus ask the user for an input, which implants are available in the present case. The system carrying out the method may thus prompt or ask for a user input on a display, but may also retrieve information from a data storage in this respect.

According to another exemplary embodiment of the present invention, the identified possible cranial positions are outside the skull avoidance zones defined in the statistical skull data.

It is understood by the skilled person from the present disclosure that the purpose and nature of the skull avoidance zones are geometrical constraints such that the result of the presented method provides one or more possible cranial positions that are not overlapping with that geometrically defined skull avoidance zones. Alternatively, the possible cranial positions/areas are not having more than an acceptable and predefined amount or percentage of overlap with said skull avoidance zones.

According to another exemplary embodiment of the present invention, the skull avoidance zones at least include a muscle area at the lateral side of the skull, a zone on the back of the skull where the skull would have contact with a bed in a lying position of the patient, a zone of the skull along which the typical hairline extends, and/or one or more statistically derived zones describing a typical position and/or a size of the inter-individually variable frontal sinus.

According to another exemplary embodiment of the present invention, the method further comprises the step of acquiring at least one of the following parameters which describe the individual patient: age, medical condition, ethnicity, type of skull, gender, and a phenotype parameter describing the skull. Furthermore, during the step of acquiring the statistical skull data, said acquired parameter or parameters describing the individual patient are taken into account.

In other words, in this embodiment it is specified that the statistical data used for the method of the present invention can be selected based on several parameters that are known from the individual patient. This may further increase the accuracy of defining optimal cranial positions for an implantation on the patient's skull.

According to another exemplary embodiment of the present invention, the method further comprises the step of determining whether the patient's skull comprises open or closed fontanelles. Moreover, using a result of the determination about the fontanelles during the step of identifying possible cranial positions is comprised.

Specifically in pediatric patients where there is no sufficient information on bone density, this additional information about the state of the fontanelles can be very important for pre-operative planning.

According to another exemplary embodiment of the present invention, the method comprises the determination of calcifications in the patient's skull. The result of this determination is then used during the step of identifying possible cranial positions.

Taking into account the parameter of calcifications during the identification of contiguous skull segments, which are safe and can reliably be used for implantation, further increases the accuracy and safety of the implantation.

According to another exemplary embodiment of the present invention, the implant is embodied as an Implantable Pulse Generator (IPG), an IPG having a non-planar, curved shape at a side facing the patient's skull when being implanted, an individualized IPG having a geometrical shape that is adapted to a shape of the individual patient's skull, or as a responsive neurostimulation (RNS) device.

In the context of deep brain stimulation, a new generation of implantable pulse generators is being brought into the market which (mostly rechargeable) are not placed in the abdominal or a chest cavity anymore but are anchored in or on top of the skull. These devices can have thicknesses of below 1 cm, however, not every skull has bone regions that are thick enough to safely accommodate the full or even partial depth of such an implant. Therefore, the computer-implemented medical method presented herein which automatically provides a pre-operative assessment of pulse generator placement in human bone is a very advantageous tool for these upcoming implants.

According to another exemplary embodiment of the present invention, the method further comprises the step of automatically identifying possible cranial positions on the patient's skull for placing a fixation frame and/or a head clamp at the patient's skull thereby taking into account the previously identified possible cranial positions for the at least one implant.

In other words, in this exemplary embodiment, the method as described herein is in a first iteration used for defining an ideal position for IPG implantation and in a second iteration, it is used for defining location for the frame fixation. During the identification of the locations for the screws of the fixation frame and/or a head clamp, the previously determined location/area for the IPG is used as an additional geometrical constraint.

According to another exemplary embodiment of the present invention, the method further comprises the step of acquiring a user input about the kind of available IPGs as implants, in particular whether a rechargeable or a non-rechargeable IPG is available.

In this embodiment, the method as described herein may take into account whether a rechargeable or a non-rechargeable IPG is available, since this may further restrict the selection of the region where the implantation can be done properly. In particular, certain areas of the skull may be excluded if only a rechargeable IPG is available in addition to the already used criteria of the skull avoidance zones. In particular, the recharging of such an IPG may use inductive loading via a device, which is placed on the outer surface of the patient's skull for recharging the IPG inside the skull. However, these circumstances are not convenient for the patient at any skull location, and hence in case of a rechargeable IPG, the method presented herein may restrict the possible regions even further.

According to another exemplary embodiment of the present invention, the method comprises the step of generating an output signal representative of a suggestion to a user containing which IPG shall be used at which position of the patient or alternatively in an abdominal or chest area of the patient.

According to another exemplary embodiment of the present invention, the implant is embodied as a plurality of fixation screws for fixing a fixation frame at the patient's skull. In this embodiment, the method further comprises the step of automatically identifying possible cranial positions on the patient's skull for each screw based on the individual patient data set and the statistical skull data thereby using geometrical descriptions of the screws.

As is apparent to the person skilled in the art, this embodiment relates to a stereotactic fixation frame with several screws entering the patient's skull at several different locations as can be seen in for example the embodiments of FIGS. 2 and 4.

According to another exemplary embodiment of the present invention, the method further comprises the step of acquiring a clinical report about the possible cranial position identified in a first iteration of the method and finally used by a user and taking said clinical report into account in a further iteration of the method as presented herein.

In this embodiment, the clinical report about a first result of the method is used and it is taken into account in an upcoming iteration of the described method. In this respect, this provides a so to say self-learning effect of the method since in subsequent iterations, the results of previous iterations are taken into account during the automatic identification of possible cranial positions.

According to another exemplary embodiment of the present invention, the step of transferring data representative of the automatically identified possible cranial positions and/or data representative of a user selection out of the automatically identified possible cranial positions to a medical navigation system and/or to an Augmented Reality display is comprised.

In this embodiment, the results of the method or a selection of the results made by the user are sent to a medical navigation system and/or an Augmented Reality display. For example, visualizing the thickness of the bone and the zones that are identified as being capable of receiving an implant under the said criteria using Augmented Reality directly over the patient's individual head is of great advantage for the user. This can be done for example prior to the head fixation or also after the implantation of an IPG.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

According to a third aspect of the present invention, a medical system is presented which comprises the at least one computer as mentioned hereinbefore. It comprises furthermore at least one electronic data storage device storing at least the data describing the identified possible cranial position. The medical system further comprises a medical device for carrying out a medical procedure on the patient, wherein the at least one computer is operably coupled to the at least one electronic data storage device for acquiring, from the at least one data storage device, at least the data describing the identified possible cranial positions. The at least one computer is further operably coupled to the medical device for issuing a control signal to the medical device for controlling the operation of the medical device on the basis of the data describing the identified possible cranial position.

A navigation system for computer-assisted surgery, which is configured for carrying out the steps of any method described herein.

In the following, definitions of some terms used in this context of the present invention are provided.

Navigation System

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

Surgical Navigation System

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

BRIEF DESCRIPTION OF THE DRAWINGS

In the following, the invention is described with reference to the appendant figures, which give background explanations and represent specific embodiments of the invention. The scope of the invention is however not limited to the specific features disclosed in the context of the figures wherein FIG. 1 schematically shows a flow diagram of the method of the present invention.

DESCRIPTION OF EMBODIMENTS

Figure 1:
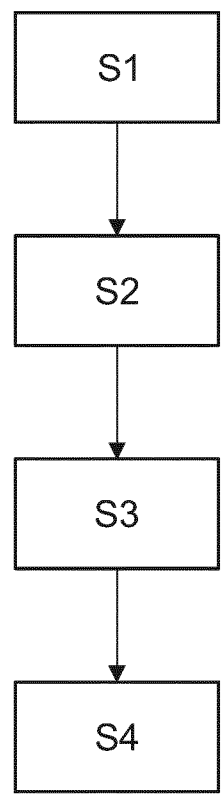

FIG. 1 illustrates the method steps of the method according to the first aspect which provides an automated preoperative assessment of implant placement in human skull. In other words, a computer-implemented medical method of identifying a cranial position for an implant in a patient's skull is presented.

In a first step S1, individual patient data are acquired which describes a bone thickness and/or a bone density of the patient's skull. Several possibilities of acquiring such data are possible and data retrieval from for example a server as well as image acquisition, auto-segmentation and bone density and thickness determination were described as exemplary embodiments thereof hereinbefore. Furthermore, in step S2, statistical skull data, which include skull avoidance zones are acquired. It is to be noted that the skull avoidance zones describe geometrical zones of the human skull, in which preferably the implant to be used shall not be implanted. Moreover, in the method of FIG. 1, a digital template data set is acquired, wherein the data set describes in a geometrical manner the at least one implant. This step is shown with reference sign S3 in FIG. 1. Based on the individual patient data set and the statistical skull data which were acquired previously in steps S1 and S2, the geometrical description of the at least one implant is used to automatically identify possible cranial positions on the patient's skull. This automatic position identification is carried out in step S4. With the method presented in FIG. 1, the medical practitioners do not have to rely on experience alone when it comes to the parameter of skull thickness in the context of for example frame placement and IPG implantation. However, the concept provided and explained for the method of FIG. 4 does also apply to any other kind of implant that shall be placed in or on the patient's skull.

The procedure defined in FIG. 1 removes uncertainty whether a given patient can safely receive an implant like for example a cranial IPG, which was previously only possible on the basis of human judgement, which of course is error-prone. It may also be beneficially applied to situations where a stereotactic frame or a Mayfield head clamp needs to be fixated at the patient's skull and thus supports the localization of optimal implant location as well as neuro-navigation guided execution of surgery. Overall, this computer-implemented medical method enhances safety and speed of such procedures.

Figure 2:
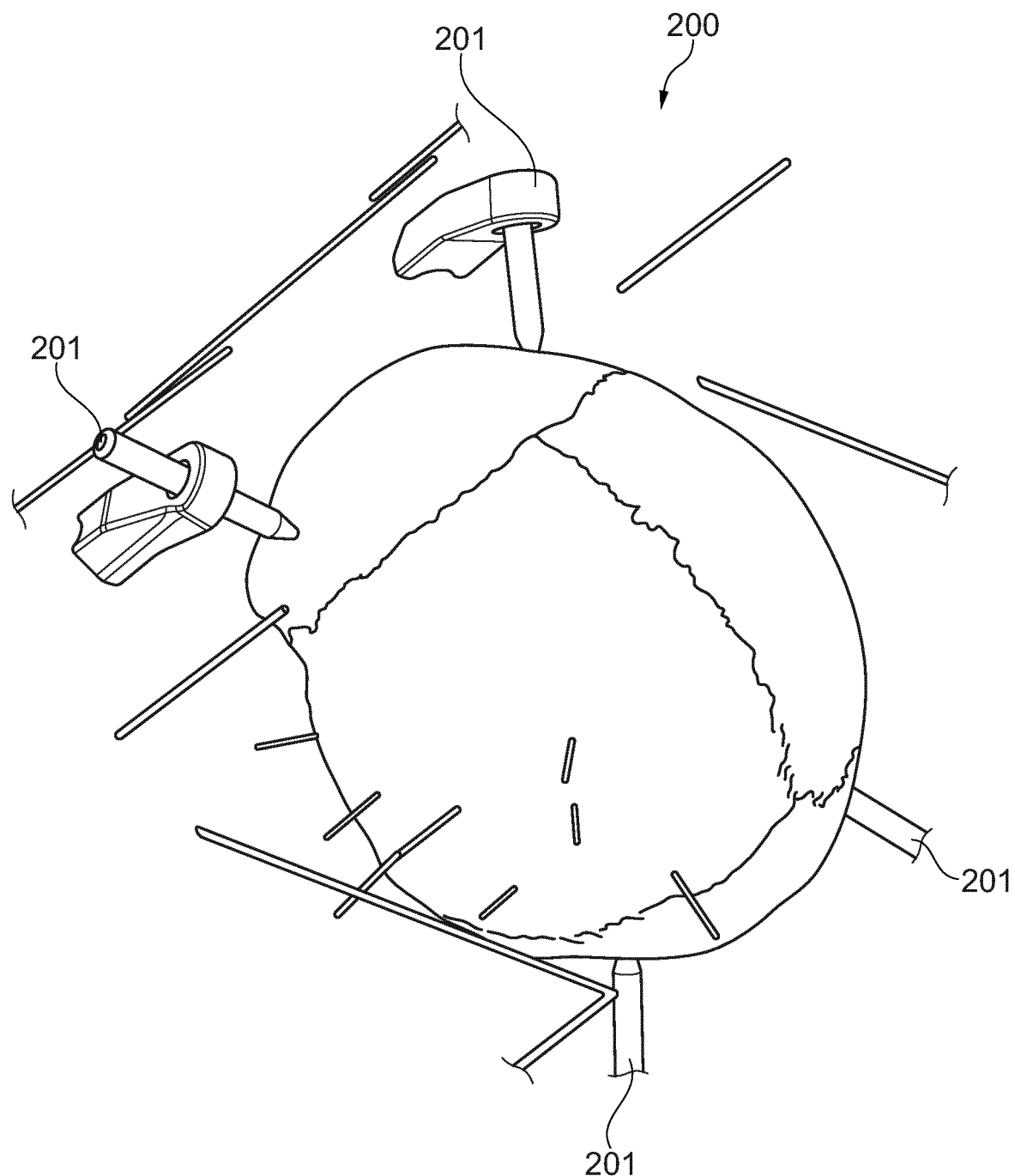
FIG. 2 schematically shows a pediatric example of a human skull with open fontanelles on which the present invention can be applied.

FIG. 2 schematically shows a visualized pediatric skull 200 with open fontanelles. Several screws 201 are shown in FIG. 2, which are inserted at specific and individual locations into the patient's skull 200. In order to define appropriate positions for the screw insertion, the method as described for example in previous FIG. 1 may be used. In an exemplary embodiment of the method described in FIG. 1, also the detection of the boundaries of the fontanelles, as can be gathered from FIG. 2, is comprised. Such boundaries or regions where the fontanelles are open are then taken into account during the automatic identification of possible cranial positions in step S4 of FIG. 1. In this way, also these boundaries of the fontanelles are to be seen as skull avoidance zones as used in the context of the present invention.

Figure 3:
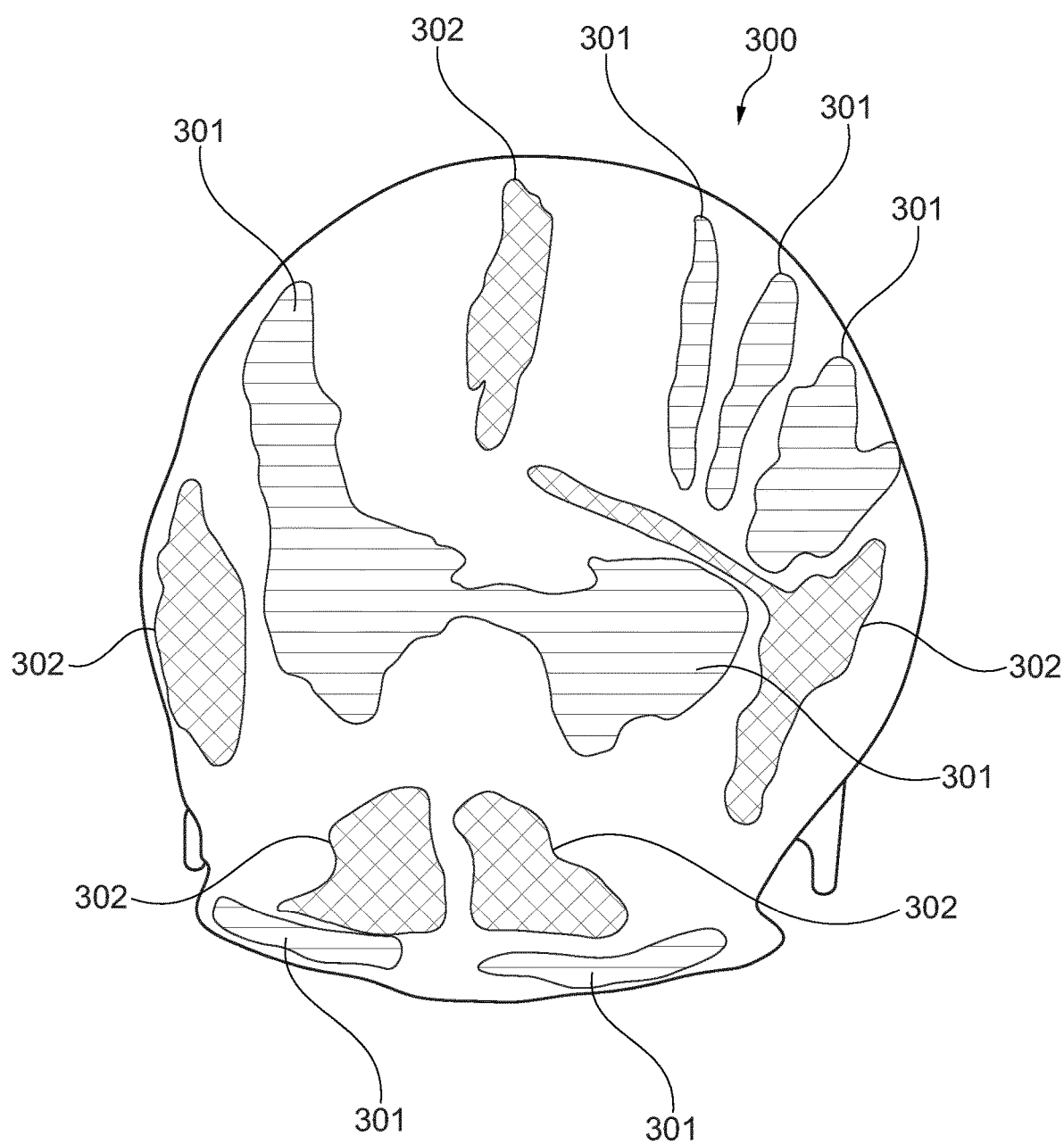
FIG. 3 schematically shows a visualized human skull of an individual patient on which several color coded regions are displayed which we identified/calculated in an exemplary embodiment of the present invention.

FIG. 3 schematically shows a skull 300 on which according to an exemplary embodiment of the present invention, certain areas on the skull are displayed to the user by color-coding. In particular, skull avoidance zones 302 are displayed to the user onto the individual patient's skull and also the result of the method presented herein, i.e. the automatically identified possible cranial positions/areas, are shown to the user by the regions 301. In an exemplary embodiment, zones 302 may be shown in e.g. red color and the identified possible cranial positions 301 may be displayed in green color. However, of course also other colors, shadings and/or optical means may be used in order to make these zones and areas distinguishable for the user. In this way, the user may then select which of the green areas 301 shall be used for finally implanting the implant. The user may in addition provide further criteria after having received this intermediate result shown in FIG. 3. For example, he may add the parameter of a minimum skull thickness under the implant to be used and the method may then further limit the green areas 301 to those areas who in addition meet the requirement of the minimum skull thickness under the implant selected.

Figure 4:
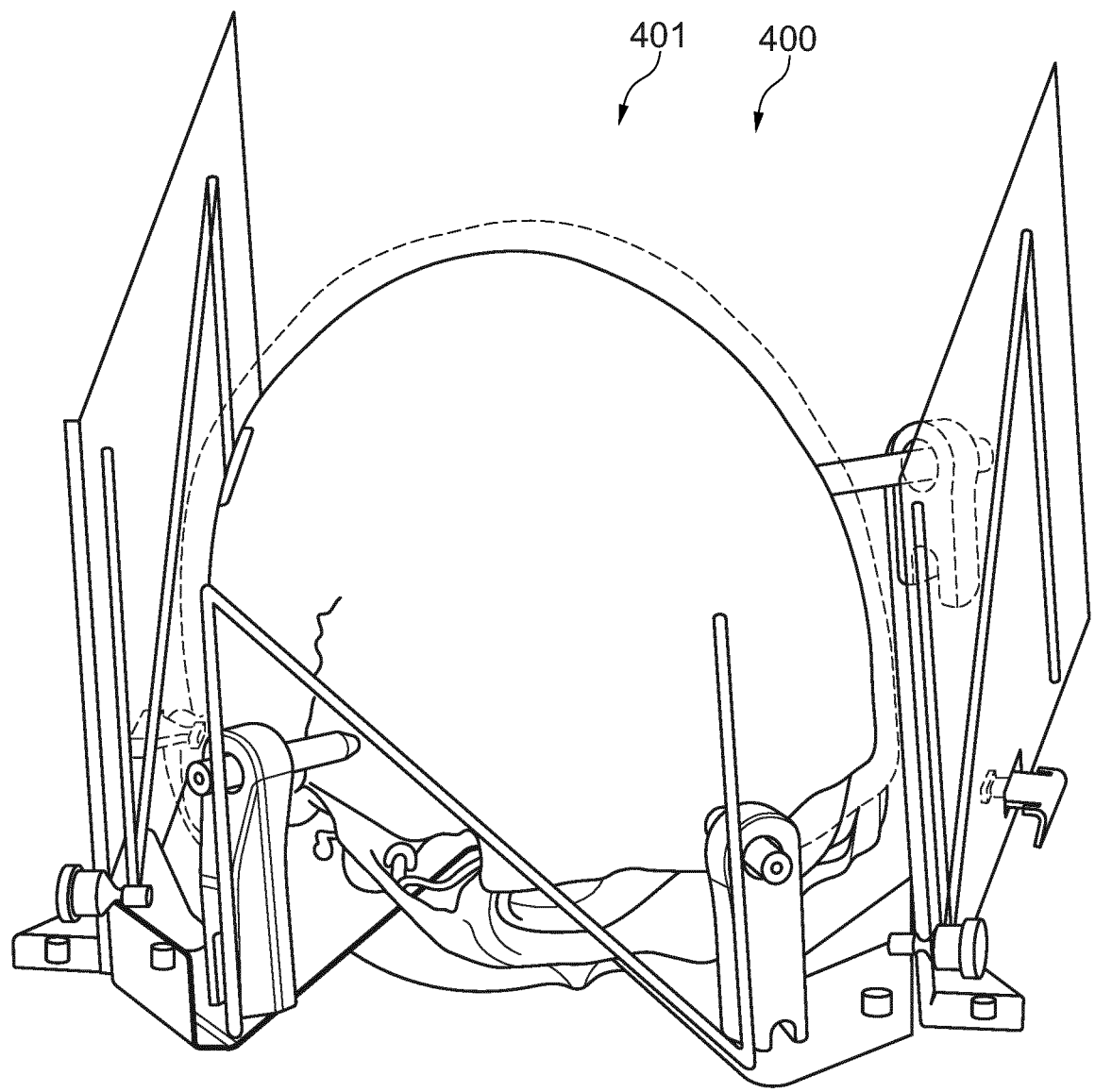
FIG. 4 schematically shows an example of a stereotactic fixation of a human skull in a fixation frame for which the present invention can be beneficially used.

FIG. 4 schematically shows a human skull 400 which is fixated as a stereotactic fixation frame 401. In such a scenario of a stereotactic radiotherapy, the method as presented herein may first be applied to find an optimal position or region to implant for example an IPG and in a second iteration of the method as described for example in FIG. 1 calculate the positions for the fixation screws of this stereotactic fixation frame 401. In other words, in an embodiment of the present invention, an automatic identification of possible cranial positions on the patient's skull for placing the fixation frame 401, or alternatively a head clamp, at the patient's skull is provided wherein thereby the previously identified possible cranial position for the at least one implant is taken into account as a further geometrical restriction. This double application of the concept of the present invention further increases the safety and reduces the risk of such an IPG implantation.

Figure 5:
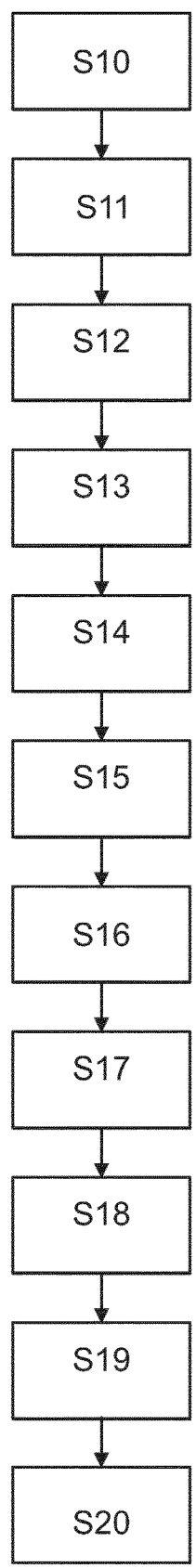
FIG. 5 schematically shows a flow diagram of an embodiment of the method of the present invention.

According to another exemplary embodiment of the present invention, FIG. 5 shows the flow diagram of a detailed computer-implemented medical method of identifying cranial positions for an implant in a patient's skull. The following embodiment cannot be used for IPGs and skull fixation in a Mayfield clamp/stereotactic frame only, but it can be also applied to other kind of implants.

In step S10, pre-operative or intra-operative CT or MRI images are acquired. Moreover, in step S11, a universal atlas automatic segmentation is run to extract the skull of the individual patient from the previously acquired images. In step S12, the skull density and skull thickness, and preferably also the fontanelles, sinuses and calcifications are detected, and it can be determined whether the fontanelles are closed or opened in pediatric cases. In step S13, statistical data is superimposed on the individual patient data set, wherein the statistical data include the skull avoidance zones. Such superimposing may make use of image fusion like for example elastic or rigid image fusion as has been explained in great detail hereinbefore. Typical examples for such skull avoidance zones are the lateral side of the skull, a zone on the back of the skull where the skull would have contact with a bed in a lying position of the patient, a zone of the skull along which the typical hairline extends, and/or one or more statistically derived zones describing a typical position and/or a size of the inter-individually variable frontal sinus.

In step S14, a user input is retrieved defining the thickness required to hold the pins for skull fixation in a Mayfield clamp/stereotactic frame. Furthermore, in step S15, a user may choose or determine which cranial IPGs are available for implantation in the individual case and also digital templates for these IPGs are provided in step S15. In step S16, a user may define or alternatively it is called from a database for each IPG a minimum skull thickness under the implant required to maintain stable skull properties. In step S17, the template fitting is attempted in the areas of the skull where the minimum skull thickness is met and which lie outside of the skull avoidance zones as described hereinbefore. Furthermore, it is displayed in step S10 whether cranial IPG implantation is safely possible for the selected implant. And if implantation is nowhere possible, a user feedback is provided and if possible, alternative IPG selections are prompted to the use via e.g. a user display of the system carrying the method of this embodiment. Moreover, in step S19, the areas are displayed where implantation can be done. Finally, in step S20, a user selected area is sent either to an IGS neuro-navigation system and/or to an Augmented Reality display to support implantation or to a robot to automatically commence milling of cranial IPG bed on a stereotactically fixated skull. As has been made clear to the skilled reader, this embodiment cannot be used for skull fixation in a Mayfield clamp/stereotactic frame only, but it can be also applied to other kind of implants.

Figure 6:
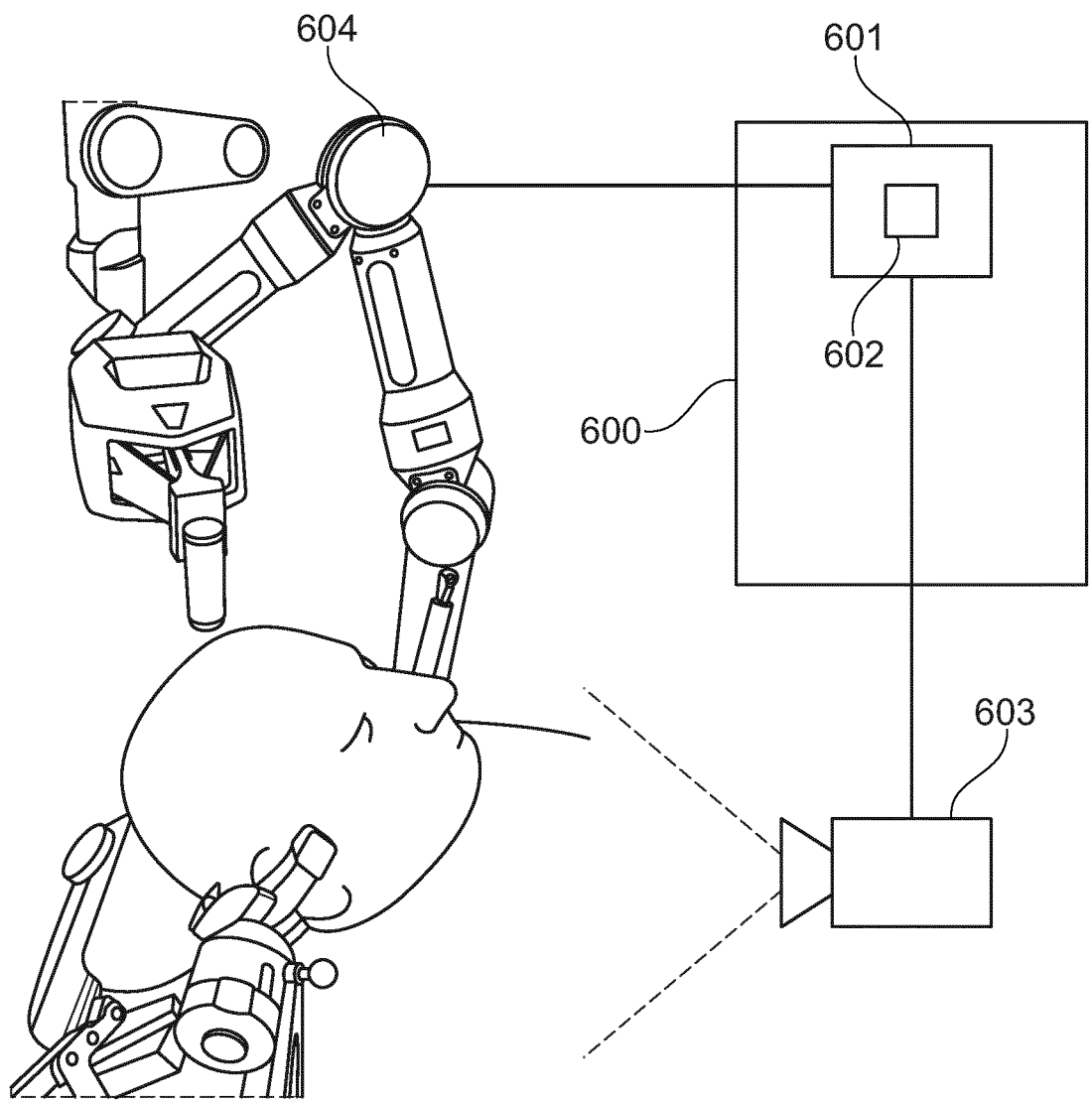
FIG. 6 schematically shows a navigation system according to an aspect of the present invention.

According to another exemplary embodiment of the present invention, FIG. 6 shows a navigation system 600 for computer-assisted surgery, which is configured for carrying out for example the steps of the method described in FIG. 1. The navigation system 600 comprises a control unit 601 and a calculation unit 602. The calculation unit 602 may be the unit, which processes and calculates the data, which is necessary for automatically identifying the cranial positions as described herein. Moreover, the control unit 601 may send signals to the robot system 604 in order to move to a particular location of the patient's skull and for example commence milling a bed for the IPG to be implanted. The embodiment of FIG. 6 further shows an optical tracking system 608, which can be used to securely control the spatial positioning of the patient's skull relative to the robot system 604.

Figure 7:
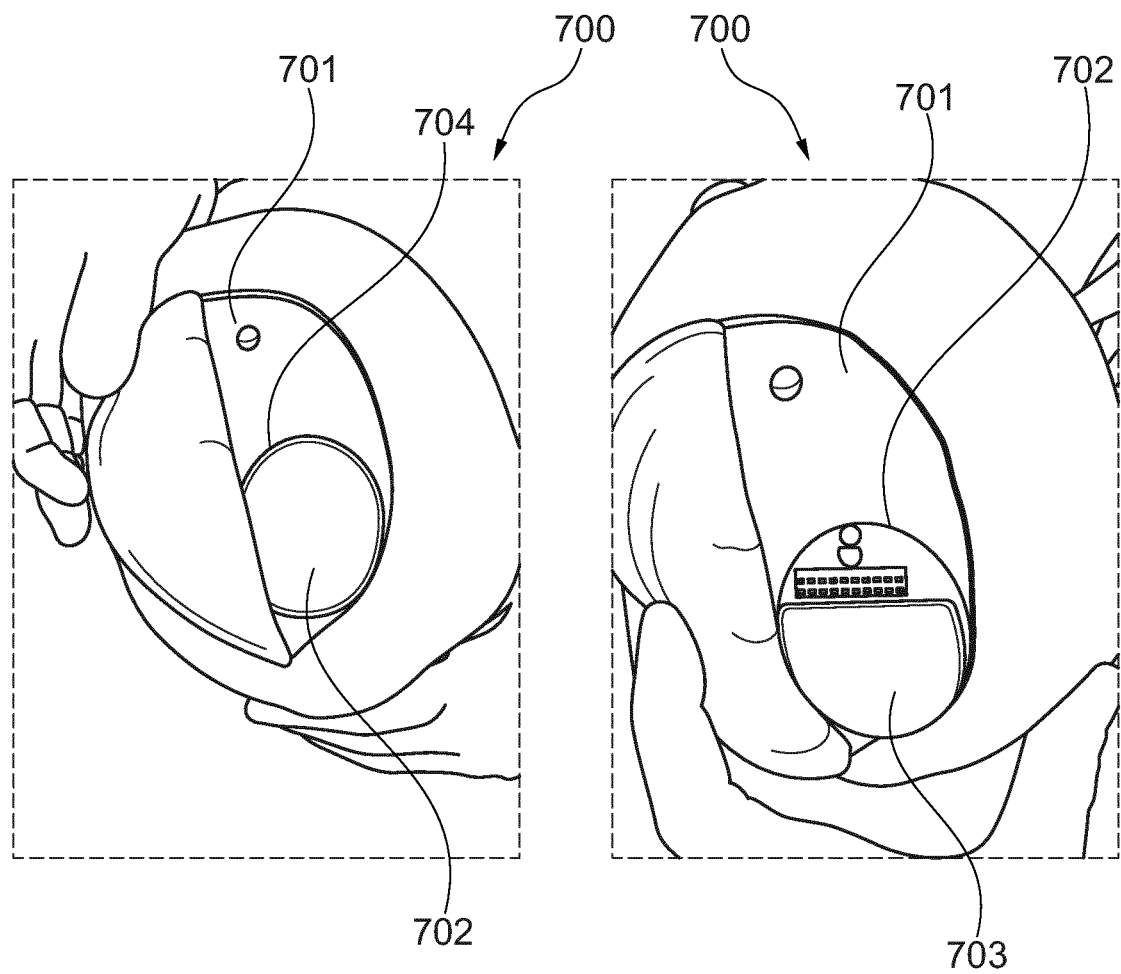
FIG. 7 schematically shows a saw bone example of a cranial IPG placement where the cranial position of the implant has been calculated according to an exemplary embodiment of the present invention.

FIG. 7 schematically shows a saw bone example 700 of a human skull on which a cranial IPG placement is to be carried out. On the left-hand side, FIG. 7 shows a picture of the skull model 700 where under the skin the skull bone 701 can be seen. 702 shows an IPG bed, which was milled into the skull 701 such that the IPG 703 can be received safely. This bed to receive the IPG 703 contains an outer boundary 704, which is the result of the method presented herein and applied to this particular embodiment of FIG. 7. In other words, the boundary line 704 shows the possible cranial position where the IPG 703 can be implanted. This data describing the outer boundary 704 may be sent to a for example milling device to mill into the skull 701 the IPG bed 702.

Further implementations are clear for the skilled person as they are in his working environment after being provided with the disclosure defined herein.

The invention claimed is:

1. A computer-implemented medical method of identifying a cranial position for an implant in a patient's skull, the method comprising the following steps:
   acquiring an individual patient data set which describes a bone thickness and/or a bone density of the patient's skull,
   acquiring statistical skull data including skull avoidance zones in which preferably no implant shall be implanted, wherein the skull avoidance zones at least include one or more statistically derived zones describing a typical position and/or a size of an inter-individually variable head anatomy, acquiring a digital template data set which geometrically describes at least one implant, and automatically identifying a possible cranial position on the patient's skull for the at least one implant based on the individual patient data set and the statistical skull data thereby using the geometrical description of the at least one implant, wherein the statistical skull data defines geometrical constraints or limitations describing geometric areas of a statistical human skull based on a plurality of individuals, which are excluded for the identification of said possible cranial position.

2. The method according to claim 1,
wherein the step of automatically identifying the possible cranial position on the patient's skull comprises a 3-dimensional template fitting of the at least one implant.

3. The method according to claim 1, the method further comprising the following step
retrieving a minimum skull thickness under the implant required to maintain stable skull properties, and/or
retrieving a minimum skull thickness required to hold the implant for skull fixation.

4. The method according to claim 3, the method further comprising the following steps
determining at least one continuous segment of the skull in which the retrieved minimum skull thickness is met, and
carrying out the step of automatically identifying the possible cranial position on the patient's skull only in said at least one determined segment meeting the minimum skull thickness.

5. The method according to claim 1,
wherein the individual patient data set and the statistical skull data are provided in form of image data, and the method further comprising the step
superimposing the individual patient data set with the statistical skull data in form of an image fusion of the individual patient data set and the statistical skull data.

6. The method according to claim 1, the method further comprising the following step
displaying the respectively identified the possible cranial position on a user interface, preferably using color coding in a graphical representation of the patient's skull.

7. The method according to claim 1, the method further comprising the following steps
acquiring CT images, MRI images and/or at least one other medical image from the patient,
extracting the patient's skull from the acquired images based on auto-segmentation, and
generating the individual patient data set by determining the bone thickness and/or the bone density of the extracted patient's skull.

8. The method according to claim 1, the method further comprising the following steps
inquiring a user input about which implant or implants are available for implantation in the individual case of the patient, and
providing digital templates of the available implants within the digital template data set.

9. The method according to claim 1,
wherein the identified possible cranial position on the patient's skull are outside the skull avoidance zones defined in the statistical skull data.

10. The method according to claim 1,
wherein the skull avoidance zones at least include a muscle area at the lateral side of the skull, a zone on the back of the skull where the skull would have contact with a bed in a lying position of the patient, a zone of the skull along which the typical hairline extends, and/or one or more statistically derived zones describing a typical position and/or a size of the inter-individually variable frontal sinus.

11. The method according to claim 1, the method further comprising the following steps
acquiring at least one of the following parameters which describe the individual patient: age, medical condition, ethnicity, type of skull, gender, and a phenotype parameter describing the skull, and
wherein for the step of acquiring the statistical skull data said acquired parameter or parameters describing the individual patient are taken into account.

12. The method according to claim 1, the method further comprising the following steps
determining whether the patient's skull comprises open or closed fontanelles, and
using a result of the determination about the fontanelles during the step of identifying the possible cranial position.

13. The method according to claim 1, the method further comprising the following step
determining whether the patient's skull contains calcifications, and
using a result of the determination about the calcifications during the step of identifying the possible cranial position.

14. The method according to claim 1,
wherein the implant is embodied as an Implantable Pulse Generator (IPG), an IPG having a non-planar, curved shape at a side facing the patient's skull when being implanted, an individualized IPG having a geometrical shape that is adapted to a shape of the individual patient's skull, or as a responsive neurostimulation (RNS) device.

15. The method according to claim 1, the method further comprising the following additional step
automatically identifying the possible cranial position on the patient's skull for placing a fixation frame and/or a head clamp at the patient's skull thereby taking into account the previously identified possible cranial position for the at least one implant.

16. The method according to claim 1, the method further comprising the following step
acquiring a user input about the kind of available IPGs as implants, in particular whether a rechargeable or a non-rechargeable IPG is available.

17. The method according to claim 14, the method further comprising the following step
generating an output signal representative of a suggestion to a user containing which IPG shall be used at which position of the patient's skull or alternatively in an abdominal or chest area of the patient.

18. The method according to claim 1,
wherein the implant is embodied as a plurality of fixation screws for fixing a fixation frame at the patient's skull, and the method further comprising the following step automatically identifying the possible cranial position on the patient's skull for each screw based on the individual patient data set and the statistical skull data thereby using geometrical descriptions of the screws.

19. The method according to claim 1, the method further comprising the following step
acquiring a clinical report about the possible cranial position identified in a first iteration of the method and finally used by a user and taking said clinical report into account in a further iteration of the claimed method.

20. The method according to claim 1, the method further comprising the following step
transferring data representative of the automatically identified possible cranial position and/or data representative of a user selection out of the automatically identified possible cranial position to a medical navigation system and/or an Augmented Reality display.

21. A non-transitory computer readable storage medium comprising instructions that when executed on at least one processor of at least one computer, causes the at least one computer to perform the steps of:
acquiring an individual patient data set which describes a bone thickness and/or a bone density of the patient's skull;
acquiring statistical skull data including skull avoidance zones in which preferably no implant shall be implanted;
wherein the skull avoidance zones at least include one or more statistically derived zones describing a typical position and/or a size of an inter-individually variable head anatomy,
acquiring a digital template data set which geometrically describes at least one implant, and
automatically identifying a possible cranial position on the patient's skull for the at least one implant based on the individual patient data set and the statistical skull data thereby using the geometrical description of the at least one implant;
wherein the statistical skull data defines geometrical constraints or limitations describing calculated geometric areas of a statistical human skull based on a plurality of individuals, which are excluded for the identification of said possible cranial position.

22. A medical system, comprising:
at least one computer having at least one processor and associated memory, the memory storing instructions which when executed cause the at least one processor to:
acquire an individual patient data set which describes a bone thickness and/or a bone density of the patient's skull;
acquire statistical skull data including skull avoidance zones in which preferably no implant shall be implanted;
wherein the skull avoidance zones at least include one or more statistically derived zones describing a typical position and/or a size of an inter-individually variable head anatomy,
acquire a digital template data set which geometrically describes at least one implant, and
automatically identify a possible cranial position on the patient's skull for the at least one implant based on the individual patient data set and the statistical skull data thereby using the geometrical description of the at least one implant;
wherein the statistical skull data defines geometrical constraints or limitations describing calculated geometric areas of a statistical human skull based on a plurality of individuals, which are excluded for the identification of said possible cranial position;
at least one electronic data storage device storing at least data describing the identified possible cranial position; and a medical device for carrying out a medical procedure on the patient, wherein the at least one computer is operably coupled to:
the at least one electronic data storage device for acquiring, from the at least one data storage device, at least the data describing the identified possible cranial position, and
the medical device for issuing a control signal to the medical device for controlling the operation of the medical device on the basis of the data describing the identified possible cranial position.

23. A computer-implemented medical method of identifying a cranial position for an implant in a patient's skull, the method comprising the following step:
acquiring an individual patient data set which describes a bone thickness and/or a bone density of the patient's skull,
acquiring statistical skull data including skull avoidance zones in which preferably no implant shall be implanted,
wherein the skull avoidance zones at least include one or more statistically derived zones describing a typical position and/or a size of an inter-individually variable head anatomy,
acquiring a digital template data set which geometrically describes at least one implant, and
automatically identifying a possible cranial position on the patient's skull for the at least one implant based on the individual patient data set and the statistical skull data thereby using the geometrical description of the at least one implant,
wherein the statistical skull data defines geometrical constraints or limitations describing calculated geometric areas of a statistical human skull based on a plurality of individuals, which are excluded for the identification of said possible cranial position, and
wherein the skull avoidance zones comprise at least one of: sides of the skull where muscles are located, the back of the skull, information that can be used describing the typical or individual hairline position to avoid aesthetic disfigurement, and statistical information on typical position and/or size of the inter-individually variable frontal sinuses.

* * * * *